United States Patent [19]
Nilsson

[11] Patent Number: 6,044,299
[45] Date of Patent: Mar. 28, 2000

[54] IMPLANTABLE MEDICAL DEVICE HAVING AN ACCELEROMETER

[75] Inventor: Kenth Nilsson, Åkersberga, Sweden

[73] Assignee: Pacesetter AB, Järfälla, Sweden

[21] Appl. No.: 09/147,999

[22] PCT Filed: Sep. 19, 1997

[86] PCT No.: PCT/SE97/01580

§ 371 Date: Jun. 24, 1999

§ 102(e) Date: Jun. 24, 1999

[87] PCT Pub. No.: WO98/14239

PCT Pub. Date: Apr. 9, 1998

[30] Foreign Application Priority Data

Sep. 30, 1996 [SE] Sweden ................................. 9603573

[51] Int. Cl.$^7$ ................................................. A61N 1/365
[52] U.S. Cl. ................................................................. 607/19
[58] Field of Search ................................ 607/9, 19, 20

[56] References Cited

U.S. PATENT DOCUMENTS

| | | |
|---|---|---|
| 4,140,132 | 2/1979 | Dahl . |
| 5,383,473 | 1/1995 | Moberg . |
| 5,447,523 | 9/1995 | Schaldach . |
| 5,496,352 | 3/1996 | Renger . |
| 5,649,968 | 7/1997 | Alt et al. .................................. 607/19 |

*Primary Examiner*—Scott M. Getzow
*Attorney, Agent, or Firm*—Hill & Simpson

[57] ABSTRACT

An implantable medical device has a housing containing an accelerometer which detects vibrations of the housing. The accelerometer generates a vibration signal in response to the detected vibrations, which is supplied to a signal processing unit. The signal processing unit generates, for each of a number of predetermined frequency ranges, a parameter value indicative of a defined attribute of the vibration signal. The signal processing unit forms a ratio between any two of these parameter values, and emits at least one status value dependent on this ratio. The status value is uniquely indicative of a predetermined type or level of cardiac activity, and the status values can be used as a control signal for controlling therapy, such as cardiac stimulation, administered by the implantable medical device.

18 Claims, 4 Drawing Sheets

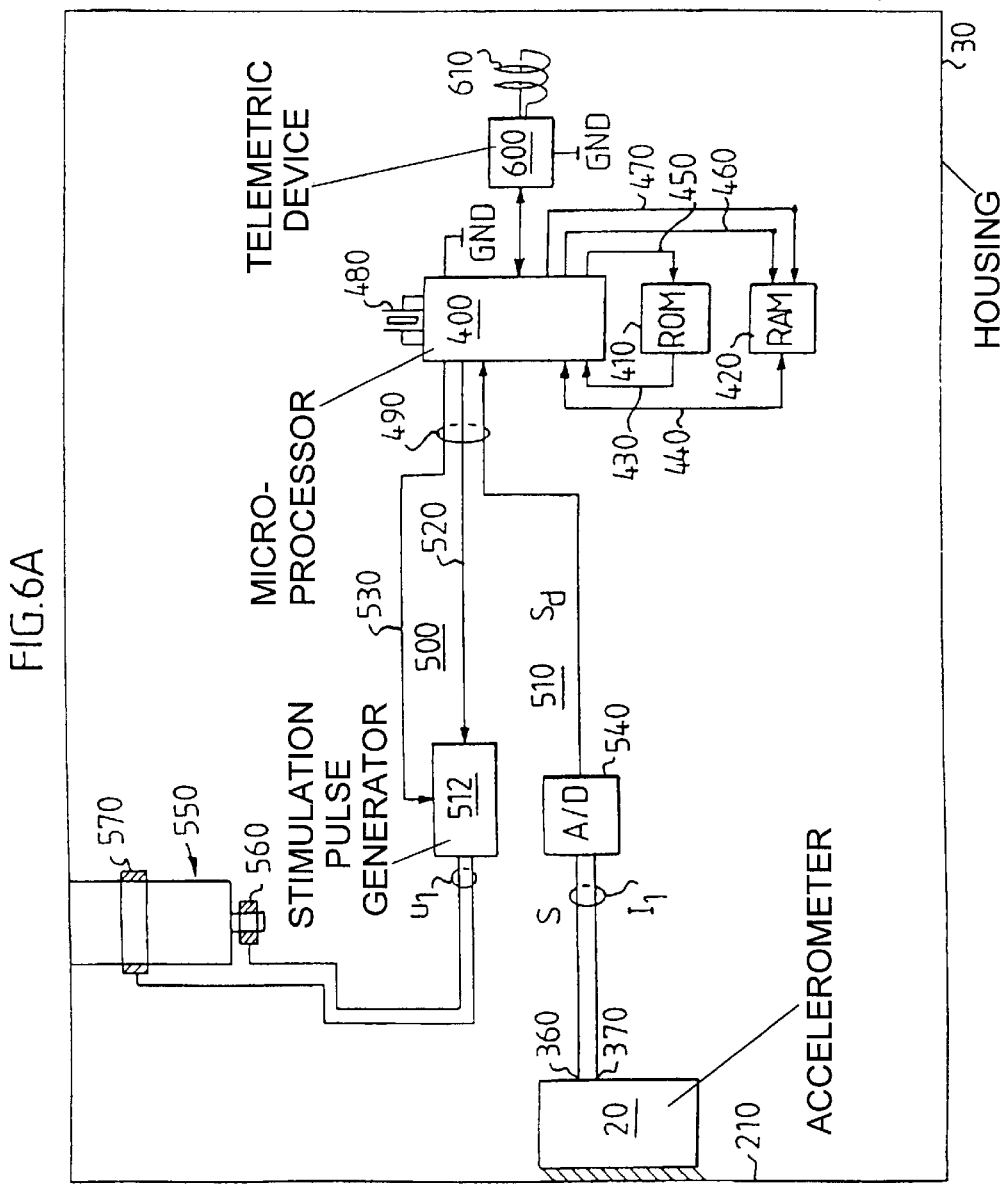

IMPLANTABLE MEDICAL DEVICE HAVING AN ACCELEROMETER

BACKGROUND OF THE INVENTION

1. Field of the Invention

The present invention relates to an implantable medical device, such as an implantable heart stimulator, of the type containing an accelerometer for detecting mechanical vibrations conducted by tissue in the vicinity of the implanted device.

2. Description of the Prior Art

From U.S. Pat. No. 4,140,132 a variable rate pacemaker is known having a piezo-electric element which, when subjected to motion, vibrates due to the resulting strain upon it to provide alternating voltage. Said voltage is used for varying the rate of the pacemaker which consequently is varied in response to the physical activity of the pacemaker patient.

Pacemakers commonly uses electrodes for sensing electrical signals related to heart activity. Alternatively a pacemaker may use sounds related to heart activity for monitoring heart activity. U.S. Pat. No. 5,447,523 discloses a pacemaker including a microphone for sensing acoustic heart signals. The microphone includes a sensor responsive to relative movement between two portions of the pacemaker housing caused by heart movements. The sensed signals are filtered and systolic time intervals (STI) are extracted from it. The systolic time intervals are used as reference quantities for the stimulation pulse rate. The amplitude of the detected sound signal is small since only the difference in movement between the two housing portions is detected. The quality of the sensed sound signal varies from patient to patient depending on the bodily constitution of the patient. These limitations need to be considered when using this prior art sensor signal for controlling a pacemaker. Furthermore, the systolic time intervals suffer from lack of sensitivity as control parameters for a pacemaker.

SUMMARY OF THE INVENTION

A primary object of the invention is to solve the above-mentioned problem that the quality of the sensed sound signal varies from patient to patient depending on the bodily constitution of the patient.

A second object is to solve the abovementioned problem related to the fact that the systolic time intervals suffer from lack of sensitivity as control parameters for a pacemaker.

A third object of the present invention also relates to the problem of providing a heart stimulator having means for generating suitable stimulation signals without the need for electrodes for electrically sensing heart activity.

The above objects are achieved in accordance with the principles of the present invention in an implantable medical device having an accelerometer mounted in an implantable housing, the accelerometer detecting vibration of the housing and generating a vibration signal in response to those vibrations, and having a signal processor contained in the housing which is supplied with the vibration signal and which generates, for a number of predetermined frequency ranges, respective parameter values which are indicative of a predetermined attribute of the vibration signal, and the signal processing unit calculates a ratio of any two of these parameter values and emits, dependent on the ratio, at least of a number of predetermined status values respectively indicating different predetermined cardiac activities.

Thus, according to the inventive device a status value related to heart activity is established as a quotient i.e., a ratio between two parameter values. The establishing of quotients leads to elimination of the disadvantageous dependence of measured values on the bodily constitution of the patient. Furthermore the quotient values are less dependent on the position of the patients body than are the parameter values as such.

According to a preferred embodiment of the device according to the invention the sensor signal is generated by a sensor means including an accelerometer having a primary direction of sensitivity substantially perpendicular to the plane of the disc shaped housing of the implantable device. This leads to an advantageously high sensitivity to heart vibrations, when the device is implanted in a subject's body as the direction of sensitivity then coincides with the direction from the device to the heart. This directivity of the sensor device also has the advantage of reducing the sensitivity to noise and tissue vibrations in other directions than those falling within the direction of sensitivity. Thereby the quality of the parameter signals and status signals is improved. Externally generated vibrations, e.g. due to physical activity of the patient are small in comparison with the heart vibrations. The device according to the invention can of course be used to measure physical activity in a rate responsive pacemaker. Generally, physical activity is normally represented by a vibration frequency of less than 20 Hz and heart sound generated vibrations has normally a frequency of more than 20 Hz. The device is easily vibrated in response to vibrations in the tissue in which it is placed when implanted, since it preferably has a weight below 20 grams. This feature, particularly in combination with the above described directivity of the sensor, leads to highly accurate status signals being provided.

A very advantageous placement of the device, giving the highest sensitivity to heart sound, is to place it directly on the heart where it can be placed either between the epicardium and the pericardium or on the pericardium.

Furthermore an implanted heart sound detector detects and registrates heart sounds with a greater accuracy than a conventional heart stethoscope does, giving very valuable information from a diagnostic viewpoint leading to a better security for the diagnosis for patients in different situations.

DESCRIPTION OF THE DRAWINGS

FIG. 6A shows a schematic block diagram of a second embodiment of the heart stimulator according to the invention.

FIG. 6B shows an extracorporeal signal processing device adapted to communicate with the pacemaker according to FIG. 6A.

DESCRIPTION OF THE PREFERRED EMBODIMENTS

Figure 1A:
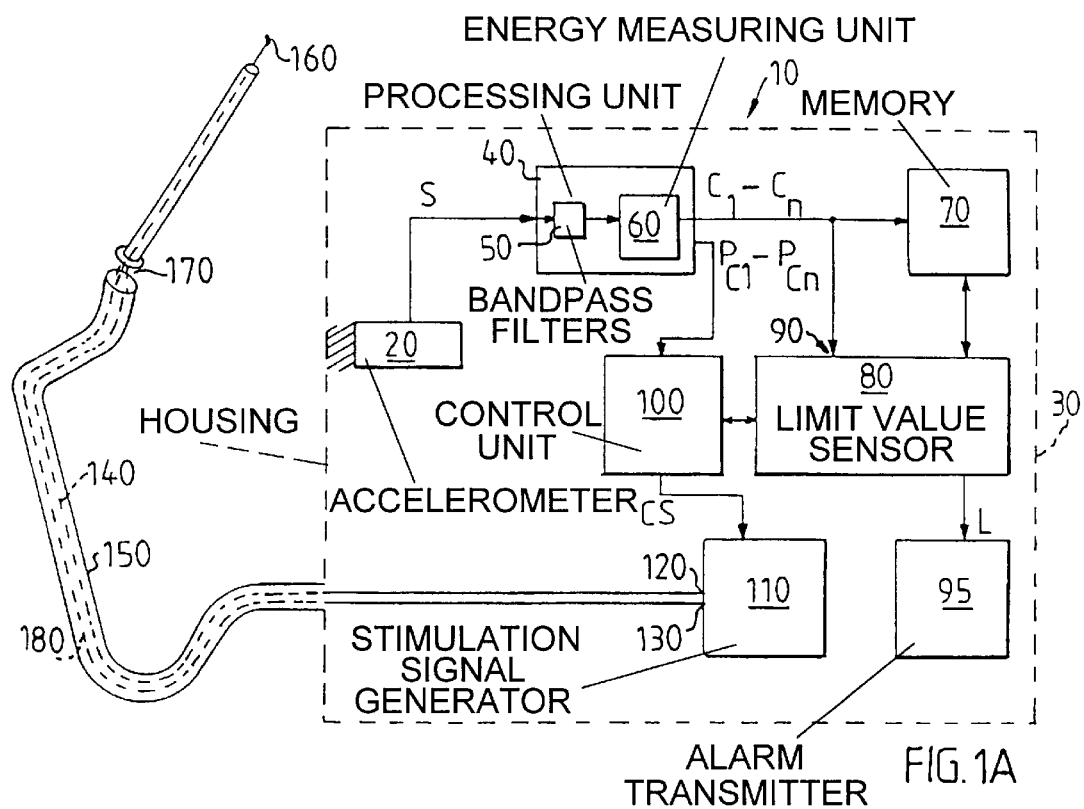
FIG. 1A shows a schematic block diagram of a first preferred embodiment of the invention.

FIG. 1A shows a schematic block diagram of a first embodiment of an implantable device 10 for providing stimulation signals and for detecting signals relating to heart activity of a patient. The device 10 includes an accelerometer 20, which is mechanically connected to the housing 30 of the stimulator 10, as will be described in detail in connection with FIGS. 2 and 3. The accelerometer 20 senses the vibrations of the pacemaker housing 30. The accelerometer 20 and the housing 30 functions together as a microphone for acoustic waves corresponding to heart valve sounds and heart muscle movements.

As clear from the above, the accelerometer produces an vibration signal S containing information about the activity of the heart. According to the invention the signal is processed such that a number of parameter values are generated indicative of the informational content of the vibration signal S. In response to the parameter values it is possible to determine the medical status of the heart.

The accelerometer 20 supplies the vibration signal S to a processing unit 40, which includes a plurality of bandpass filters 50 for dividing the electrical signal S into a plurality of frequency bands $B_1$–$B_n$, the frequency bands having the center frequency at e.g. 50, 100, 200 and 400 Hz. However other center frequencies, both higher and lower ones are possible depending on the frequency of interest. A unit 60 is arranged for measuring the respective energy $P_1$–$P_n$ in the frequency bands $B_1$–$B_n$ for generating a reference value $P_{r01}$, which is the total amount of energy calculated as the sum of $P_1$–$P_n$, and for dividing each individual energy value $P_1$–$P_n$ with the reference value so as to achieve a number of parameter values $C_1$–$C_n$. The energy values $P_1$–$P_n$ are sampled with a sampling frequency $f_s$, which may be, for example, 2 kHz. Accordingly, n digital energy signals will be generated, each signal indicating the actual sensed energy within a specified frequency band.

The parameter values $C_1$–$C_n$ are supplied to a control unit 100 where a set of status values are determined as a quotient between two simultaneously generated parameter values. The control unit is in FIG. 1 shown as a separate unit but could as well be an integral part of the processing unit 40. Each parameter value constitutes a value indicative of the amount of vibration of the stimulator housing in the respective frequency region. The relation between the amplitudes in two different frequency regions expressed as quotients (ratios) could be selected as:

$$Q_1 = C_1/C_2$$

$$Q_2 = C_2/C_3$$

where the values of $Q_1$, $Q_2$ etc. are indicative of the status of the heart. The parameter values forming the quotient (e.g. $C_1$ and $C_2$) are chosen in dependence on which conditions to be studied, e.g. valve sounds and heart muscle movements from heart tissue close to the pacemaker housing. The heart's contractility is, for example reflected by the frequency content of the heart sound in the way that a heavier heart contraction is shown as a frequency shift towards higher frequencies.

The normal values for the quotients constitute reference status values in response to which a first operational mode of the heart stimulator may be suitable. Such normal values are stored in a memory 70.

The control unit operates to monitor the new status values in realtime. By means of registering a predefined deviation from the stored reference status values another operational mode for the heart stimulator can be activated. A stimulation control signal CS is generated in response to these comparisons made in the control unit 100. As indicated above the heart's contractility can be determined from the detected heart sound, and then also other parameters related to the contractility, e.g. the stroke volume, blood pressure (P) and dP/dt. These parameters can be used by the control unit to decide which operational mode the heart stimulator should work in. Using one or many of these parameters as a control parameter for a pacemaker is well known by a person skilled in the art of pacemakers and therefore is not described in this application.

The parameter values $C_1$–$C_n$ can also be supplied to the memory 70 for storage in consecutive time order and to a limit value sensor 80. The limit value sensor 80 is operative to provide comparisons between the actual parameter values received on a first input 90 from the signal processing unit 40 with reference parameter values stored in the memory 70. According to one version of the invention the limit value sensor 80 generates a moving average value $C_{1a}$–$C_{na}$ of each of the parameter values $C_1$–$C_n$. The moving average value is calculated as the average value for each of the parameter values during a floating time window comprising predetermined consecutive parameter values. The limit value sensor compares the actual parameter value $C_1$ with the moving average $C_{1a}$ and if one or several of the actual parameter values $C_1$–$C_n$ deviate by more than a predetermined amount from the corresponding moving average the limit value sensor 80 generates an alarm signal L.

The alarm signal L is supplied to an alarm transmitter 95. Alternatively the alarm signal L may be stored in the memory 70 so as to be readable for example by means of telemetry at a later point in time when the patient visits a doctor.

The signal processing unit 40 also provides a continuous energy signal having an amplitude corresponding to the actual energy within each respective frequency band. Accordingly the signal processing unit provides n energy signals $P_{c1}$–$P_{cn}$ to a control unit 100. The control unit 100 operates to generate a stimulation control signal in response to the energy signals. The stimulator control signal CS is provided to a stimulation signal generator 110. The signal generator 110 comprises a signal output 120 and a reference output 130. The signal output 120 is coupled to a conductor 140 in an implantable lead 150 having a tip electrode 160 which is connected to the conductor 140. The lead 150 also has a ring electrode 170 which is connected to a conductor 180 in the lead 150. The conductor 180 is coupled to the reference output 130. Accordingly the stimulator signal potential provided between terminals 120 and 130 will result in a corresponding electric potential between tip electrode 160 and ring electrode 170. According to another version of the device according to the invention the output 120 is coupled to a lead having only one electrode and the reference terminal 130 is coupled to the housing 30 which is electrically conductive and which functions as a reference electrode.

Figure 1B:
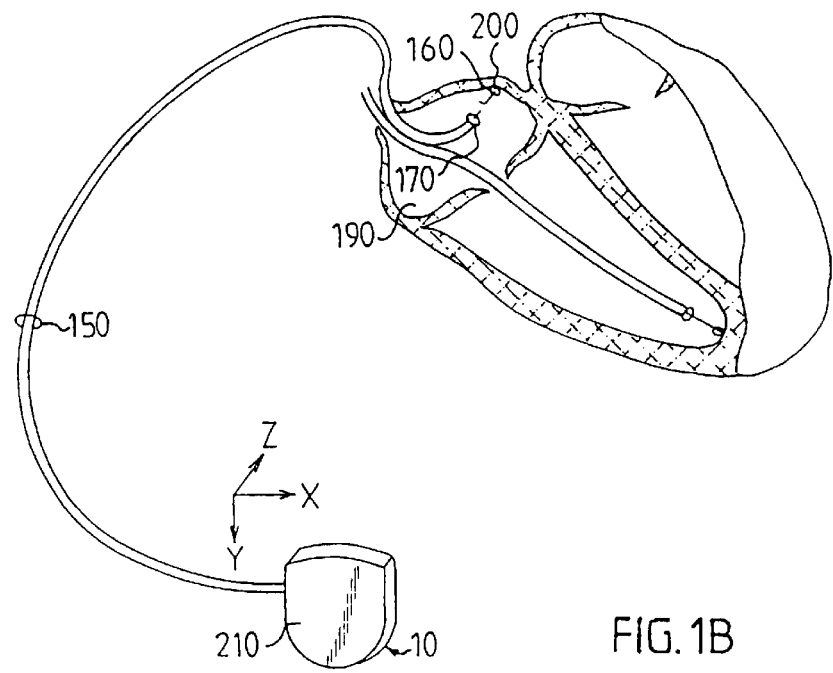
FIG. 1B is a perspective view of a heart stimulator shown implanted in association with a heart for pacing.

Referring now to FIG. 1B, there is shown a simplified representation of two ways that an implanted pacemaker 10 may make electrical contact with the heart of the patient.

FIG. 1B reflects the use of a bipolar lead 150 being directed into the right atrium 190 of the heart. The distal tip electrode 160 is typically placed in a cavity of the right atrium 190 referred to as the atrial appendage 200. The housing 30 of the stimulator device 10 is substantially disc shaped with one side wall 210 positioned in the plane defined by the two orthogonal axes x and y in FIG. 1B. The side wall 210 has an area of preferably 500 mm$^2$. When the stimulator 10 is implanted as shown in FIG. 1B such that a normal to the wall 210 is substantially directed towards the heart of the patient, as indicated by the vector z in FIG. 1B, the direction z coincides with the maximum sensitivity direction of the accelerometer 20.

Figure 2:
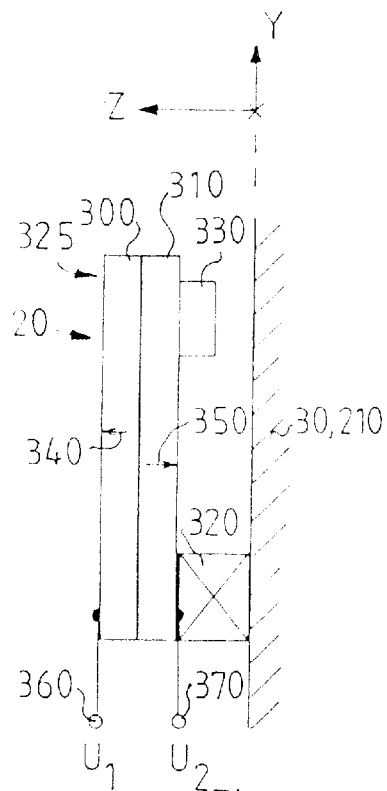
FIG. 2 is a sectional side view of an embodiment of a detector, which may be used in the device according to FIG. 1B as seen in the direction of vector x in FIG. 1B.
Figure 3:
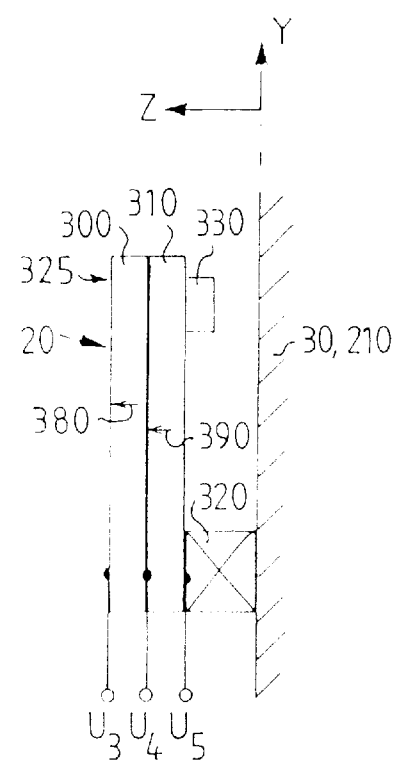
FIG. 3 is a sectional side view of an alternative embodiment of the detector.

FIGS. 2 and 3 show two alternative embodiments of the accelerometer 20 in the device according to the invention. Both of the shown embodiments comprise two elongated members of piezoelectric material 300 and 310 which are attached to each other and arranged in an aligned fashion next to each other so as to form an elongated sensor body. One end of the elongated sensor body is attached to the housing 30 (FIG. 1A and FIG. 1B) by a mount 320. The direction of elongation of the elongated sensor body 300, 310 is substantially parallel to the wall 210 of the housing 30. The elongated sensor body also has a moveable end 325, which is provided with a weight 330. Since the sensor body is attached to the housing 30 only at the one end the inertia of the weight 330 will cause the sensor body to bend in response to accelerations of the housing 30. Accordingly, when the stimulator device is implanted in the body of the patient in a manner shown in FIG. 1B the free end 325 of the sensor body will move in a direction substantially parallel with the direction of the normal z to the surface of the wall 210.

The elongated members 300 and 310 are polarized in substantially opposing directions as indicated by arrows 340 and 350 in FIG. 2. When the sensor body moves as described above an electrical signal S is provided between terminals 360 and 370.

According to the alternative embodiment of the accelerometer 20 (FIG. 3) the two elongated elements 300 and 310 are polarized in the same direction as indicated by arrows 380 and 390. A first electric sensor signal is provided between terminals $U_3$ and $U_4$ while a second electric signal is provided between terminals $U_4$ and $U_5$. By means of an adding amplifier or other suitable means the two signals are transformed into one sensor signal S.

The electrical vibration signal S is divided into one signal for each frequency band as described above.

Figure 4:
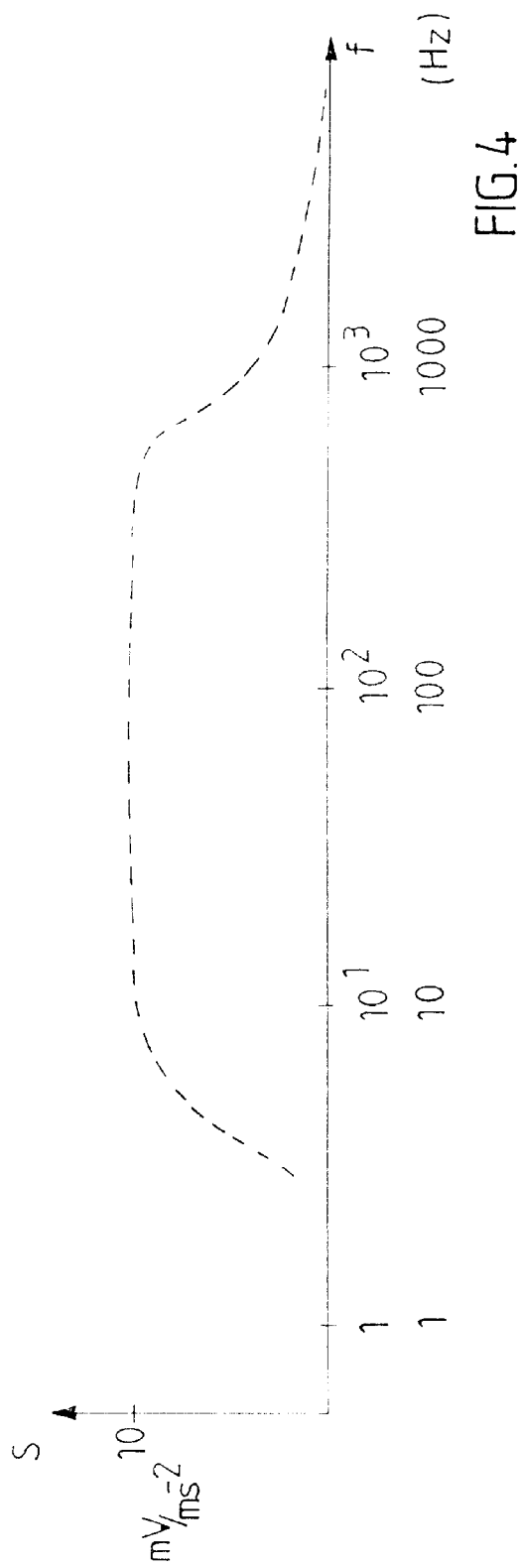
FIG. 4 is a frequency/amplitude diagram illustrating the sensitivity of the detector shown in FIG. 2 or 3.

The accelerometer shown in FIGS. 2 and 3 has a sensitivity of about 100 millivolts per g, that is roughly 10 millivolts per ms$^{-2}$ for vibrations having a frequency between 20 hertz and 600 hertz. A typical frequency response curve for an accelerometer according to FIG. 2 is shown in FIG. 4.

Placing the accelerometer 20 in contact with the housing 30 enables the accelerometer to provide a sensor signal in response to the movements of the stimulator 10. This means that the vibration signal S depends on the vibrations of the heart stimulator 10.

The stimulation device 10, when implanted, functions to measure the activity of the heart of the patient by sensing mechanical vibrations transmitted by body tissue to the housing of the device 10. A fundamental problem related to all measurements is to minimize the influence of the measurement tool on the object to be measured. The inventor realized that in the case of accurately measuring vibrations in body tissue, this problem is transformed into the problem of providing a device having a housing with shape, size and weight such that damping of the vibrations is minimized.

Tests for determining the influence of the weight of the stimulator 10 on the sensitivity indicate that when the weight of the stimulator 10 is below 50 grams the sensitivity reaches acceptable values. The sensitivity is particularly favourable when the weight of the stimulator 10 is below 20 grams. According to a preferred embodiment of the invention the stimulator 10 has a weight W in the range from 13 to 17 grams.

Tests for determining the influence of the disc-shaped side wall area of the stimulator 10 on the sensitivity indicate that when the side wall area of the stimulator 10 is below 1500 mm$^2$ for adults the sensitivity reaches favourable values. The measurement sensitivity to high frequency vibrations, i.e. above 400 Hz, increases when the side wall area is decreased. According to a preferred embodiment the stimulator device 10 has a side wall area of 500 mm$^2$ for adults.

The results of the tests indicate that the vibration signal S is advantageously accurate when the quotient of the weight W and the side wall area has a value below 0.05 g/mm$^2$, for adults provided that the side wall area is kept below 1000 mm$^2$.

Figure 5:
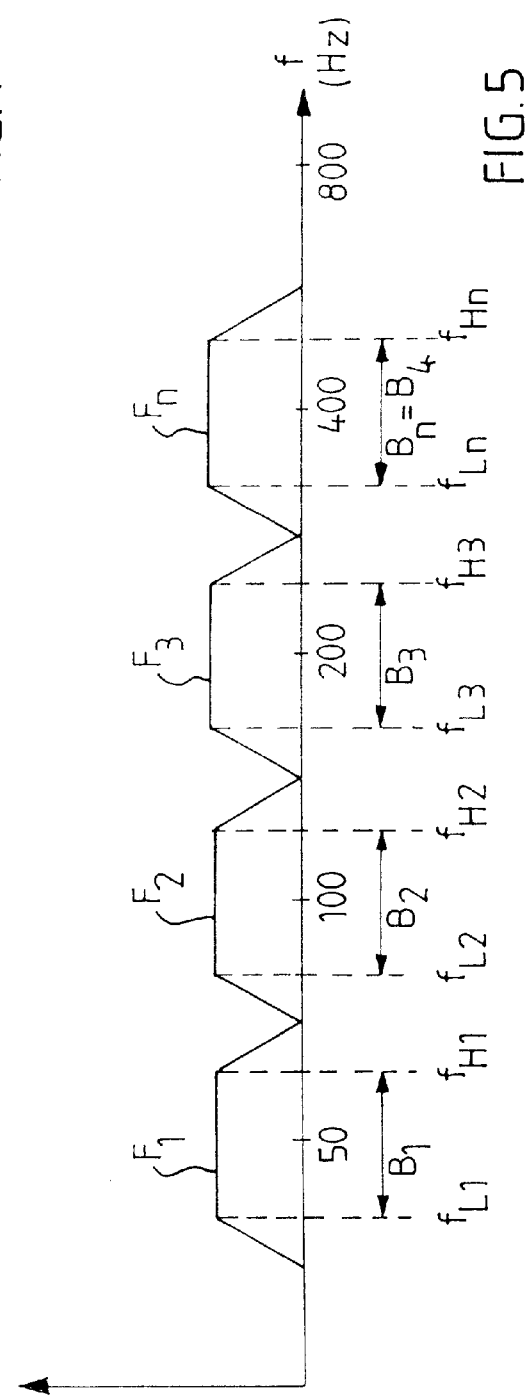
FIG. 5 is a frequency/amplitude diagram illustrating the method of dividing the sensor signal into a number of frequency bands.

As described above referring to FIG. 1, a number of bandpass filters 50 are used for dividing the vibration signal S into a plurality of indicator signals $S_1$–$S_n$. Each indicator signal has a bandwidth corresponding to the three dB bandwidth of the corresponding bandpass filter. In FIG. 5 the fall lines illustrates the frequency response for the filters F1–Fn, having bandwidths $B_1$–$B_n$. The number of frequency bands is arbitrary but there should be at least three frequency bands. All frequency bands are within the frequency range where vibration signals are related to heart sound. According to a preferred embodiment the frequency range of the vibration signal S is between 0.2 hertz to 1000 hertz.

A block diagram of a pacemaker body including electronic circuitry in accordance with a second preferred embodiment of the invention is shown in FIG. 6A. The pacemaker 10 comprises a hermetically sealed housing 30. The pacemaker includes among other things a microprocessor 400 which is coupled to a read only memory, ROM, 410 and a read/write-memory, RAM, 420 via data busses 430, 440 and address busses 450, 460. There is also a lead 470 from the microprocessor 400 to the RAM 420 for setting the RAM 420 in a selected write mode or a selected read mode. A computer program is stored in the ROM 410. and by means of this program the function of the pacemaker 10 is controlled. When, in the following, it is stated that the microprocessor 400 executes a certain function it is to be understood that the microprocessor executes a certain part of the program stored in the memory 410 using data stored in the memory 420.

A clock signal generator 480 provides a clock signal to the microprocessor and also thereby provides a time reference for the pacemaker. The microprocessor 400 comprises a plurality of input/output terminals 490 coupled to two signal channels 500, 510. The channel 500 is an output channel suitable for providing stimulation pulses to the heart. The channel 500 comprises a stimulation pulse generator 512 having an output $U_1$. The pulse generator 512 is coupled to a corresponding output from the microprocessor 400 via a conductor 520, and the pulse generator 512 is arranged to produce a stimulation pulse in response to a signal provided from the output of the microprocessor. Digital data for determining for example the shape of the stimulation pulse, such as the amplitude and the duration is provided to the pulse generator 512 via a lead 530 from the microprocessor 400.

The channel 510 contains an analog-to-digital (A/D) signal converter 540 having an input $I_1$ for receiving an electrical signal corresponding to a detectable activity from the accelerometer 20. The output of the A/D converter provides a digital signal $S_d$ which is provided to a corresponding input of the microprocessor 400 via a databus.

The pacemaker 10 also has a first connector part having a socket 550 for mating with a corresponding second connector part provided at one end of an implantable lead, such as the above described lead 150, see FIG. 1B. The socket 550 has a pin socket 560 and a connector ring 570.

The microprocessor 400 is coupled to a telemetric device 600 capable of transmitting and receiving data. The telemetric device 600 comprises an antenna 610 for communicating with a corresponding extracorporeal telemetric device.

FIG. 6B shows an extracorporeal data processing arrangement having an antenna 620 coupled to a telemetric device 630 for enabling communication with an implanted telemetric device such as the above described device 600. The telemetric device 630 is coupled to a computer unit 640 comprising a data processing unit 650, an input/output device 660, such as a keyboard, and an output device 670 such as a screen.

By means of executing a fourier transform of the input signal $S_d$ the microprocessor can establish an amplitude value for a chosen frequency at a particular point in time.

Figure 7:
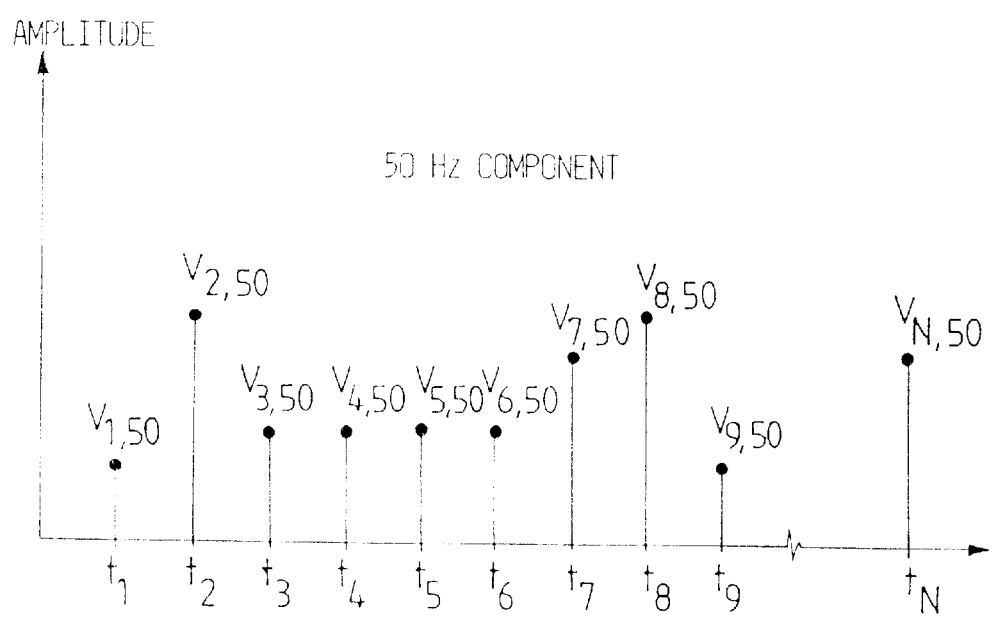
FIG. 7 is a time/amplitude diagram illustrating parameter values in the shape of sampled values indicating the temporal progression of the 50 hertz component of a sensor signal.

According to the second preferred embodiment the microprocessor establishes a set of such amplitude values at consecutive points of time (t=1, 2, ... N) for the 50 hertz component of the signal $S_d$. These consecutive values are represented in FIG. 7 as $V_{1,50}, V_{2,50}, V_{3,50}, V_{4,50} \ldots V_{N,50}$.

In the same manner, a set of amplitude values are established for the same points of time for the following frequency components: 100, 200 and 400 hertz.

Hence, digital representations of the 50, 100, 200 and 400 signal components are generated.

Each amplitude value constitutes a parameter value indicative of the amount of vibration of the stimulator housing in the respective frequency region. When, for example the heart of the patient is healthy there is a certain relation between the amplitudes in two different frequency regions. Accordingly a typical value for the quotient $$Q_{1:400,50} = V_{1,400}/V_{1,50}$$

when the patient's heart is healthy will be altered to another value indicative of different heart conditions, e.g. valve sounds and heart muscle movements from heart tissue close to the pacemaker housing, if the patient's heart condition changes.

The normal values for the quotients constitute reference status values in response to which a first operational mode of the heart stimulator may be suitable. Such normal values are stored in the memory means 410 or 420, see FIG. 6A.

The processor operates to monitor the new status values in realtime. By means of registering a predefined deviation from the stored reference status values another operational mode for the heart stimulator can be activated.

By means of the telemetric device 600, 610 the registered status values may be transmitted to the extracorporeal data processing arrangement 640, cf. FIG. 6B. The parameter values and the status values may be a useful information for helping a doctor in establishing the type of heart condition of a patient.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable medical device comprising:
   a housing adapted for implantation in a subject;
   an accelerometer mounted in said housing for detecting vibrations of said housing, said accelerometer generating a vibration signal, having an amplitude and a frequency, in response to said vibrations; and
   a signal processing unit in said housing, supplied with said vibration signal, which generates, for a number of predetermined frequency ranges, respective parameter values indicative of a predetermined attribute of said vibration signal, and which calculates a ratio of any two of said parameter values, and which emits, dependent on said ratio, at least one of a number of predetermined status values respectively indicating different predetermined cardiac activities.

2. An implantable medical device as claimed in claim 1 wherein said signal processing unit generates said parameter values as being indicative of respective amplitudes of said vibration signal in said frequency ranges.

3. An implantable medical device as claimed in claim 1 wherein said signal processing unit generates said parameter values as being indicative of respective relative amplitudes of said vibration signal in said frequency ranges.

4. An implantable medical device as claimed in claim 1 wherein said signal processing unit generates said parameter values as being indicative of respective energies of said vibration signal in said frequency ranges.

5. An implantable medical device as claimed in claim 1 wherein said signal processing unit generates said parameter values as being indicative of respective relative energies of said vibration signal in said frequency ranges.

6. An implantable medical device as claimed in claim 1 wherein said signal processing device emits at least one of said plurality of predetermined status values at successive points in time, to produce a chronological progression of said status values.

7. An implantable medical device as claimed in claim 1 further comprising a memory for storing said parameter values.

8. An implantable medical device as claimed in claim 1 further comprising a memory for retrievably storing said status values.

9. An implantable medical device as claimed in claim 1 wherein said device has a weight equal to or less than 20 grams.

10. An implantable medical device as claimed in claim 1 wherein said device has a weight in a range between 10 grams to 20 grams.

11. An implantable medical device as claimed in claim 10 wherein said sidewall of said housing has a sidewall area of less than 1500 mm$^2$.

12. An implantable medical device as claimed in claim 1 wherein said housing has a sidewall on which said accelerometer is mounted, and wherein said accelerometer has a primary direction of sensitivity substantially perpendicular to said sidewall.

13. An implantable medical device as claimed in claim 12 wherein said accelerometer comprises a sensor body having a first portion which is mechanically connected to said sidewall of said housing and a second portion attached to a movable mass element for deforming said sensor body in response to inertial forces, said sensor body producing said vibration signal in response to deformations thereof.

14. An implantable medical device as claimed in claim 13 wherein said sensor body comprises an elongated body having a first end comprising said first portion and a second end comprising said second portion, and said elongated body including at least one polarized piezoelectric transducer extending along said elongated body.

15. An implantable medical device as claimed in claim 12 wherein said sidewall of said housing has a sidewall area in a range between 250 mm$^2$ to 1,000 mm$^2$.

16. An implantable medical device as claimed in claim 12 wherein said device has a weight and wherein said sidewall has a sidewall area, and wherein said weight and said sidewall area have a ratio below 0.05 g/mm$^2$.

17. An implantable medical device as claimed in claim 1 further comprising a stimulation signal generator and an electrode connected to said stimulation signal generator and adapted to deliver stimulation signals from said stimulation signal generator in vivo to a subject, and wherein said stimulation signal generator is supplied with said at least one of said plurality of predetermined status values and said stimulation signal generator emitting stimulation signals dependent thereon.

18. An implantable medical device as claimed in claim 17 further comprising a comparator, supplied with said at least one of said plurality of predetermined status values emitted by said signal processing unit, and for comparing said at least one status value to a reference value, and for causing said stimulation signal generator to alter emission of said stimulation signals dependent on a deviation of said at least one status value from said reference value.

* * * * *